United States Patent [19]
Brimberg et al.

[11] Patent Number: 5,296,241
[45] Date of Patent: Mar. 22, 1994

[54] THERAPEUTIC COMPOSITION AND METHOD OF USING SAME FOR TREATMENT OF HANGOVER

[76] Inventors: Barnett J. Brimberg, 427 Expositions Blvd., New Orleans, La. 70118; Burde L. Kamath, 3021 Illinois Ave., Unit B, Kenner, La. 70065

[21] Appl. No.: 679,731

[22] Filed: Apr. 3, 1991

[51] Int. Cl.$^5$ ............... A61K 33/06; A61K 33/12; A61K 33/10; A61K 31/16
[52] U.S. Cl. .................. 424/682; 424/683; 424/687; 514/629; 514/574
[58] Field of Search .......... 514/630, 629, 574; 424/682, 683, 687

[56] References Cited

U.S. PATENT DOCUMENTS

| | | | |
|---|---|---|---|
| 3,829,569 | 8/1974 | Rice | 424/232 |
| 4,115,576 | 9/1978 | Penn | 424/251 |
| 4,368,206 | 1/1983 | Revici | 424/312 |
| 4,496,548 | 1/1985 | Moldowan et al. | 514/27 |
| 4,565,689 | 1/1986 | Revici | 424/10 |
| 4,593,020 | 6/1986 | Guinot | 514/159 |
| 4,703,045 | 10/1987 | Guinot | 514/159 |
| 4,704,269 | 11/1987 | Korab | 424/44 |
| 4,816,439 | 3/1989 | Jorgensen | 514/12 |
| 4,870,057 | 9/1989 | Chiapparelli et al. | 514/23 |
| 4,942,039 | 7/1990 | Duvall et al. | 424/466 |

OTHER PUBLICATIONS

Metwally, S. A., et al., J. Drug. Res. Egypt. 18(1-2):1-15-122, 1989 (Abstract).
Ali, H. M. et al., Int. J. Pharm. 42 (Mar.):155-159, 1988 (Abstract).
Orr, N. A. et al., Pharm. J. 224:547-550, 1980 (May 10) (Abstract).
Moolenaar, F. et al., Pharm. Weekbl. Sci. Ed. 1:25-30, 1979 (Feb. 23) (Abstract).

Primary Examiner—Frederick E. Waddell
Assistant Examiner—M. Moezie
Attorney, Agent, or Firm—Emrich & Dithmar

[57] ABSTRACT

A therapeutic composition for treating the manifestations of overindulgence in alcohol includes effective amounts of acetaminophen, one or more antacids agents and caffeine, all provided in finely powdered form suspended in a medium including glycerin, xanthan gum and purified water, along with a dissolved simple sugar, such that the composition is basic and has a pH less than 9. The use of a flavorant, a colorant, a stomachic and preservatives in the composition is disclosed. A method of oral administration of the composition is also disclosed.

20 Claims, No Drawings

THERAPEUTIC COMPOSITION AND METHOD OF USING SAME FOR TREATMENT OF HANGOVER

BACKGROUND OF THE INVENTION

1. Field of the Invention

The present invention relates to therapeutic compositions, particularly non-prescription compositions and methods of administering same for treatment of hangover as a result of overindulgence in alcohol.

2. Description of the Prior Art

The major symptoms of the condition generally known as "hangover" resulting from overindulgence in alcohol, include headache, acid indigestion, queasiness or nausea, diarrhea, lethargy and a general malaise. These symptoms have been treated by various techniques, generally aimed at relief of only one or a few of the symptoms. At least one formulation, designed for relief of all of the symptoms, is disclosed in U.S. Pat. No. 3,829,569. However, that formulation must be administered in two separate portions. This is because the ingredients are such that the necessary quantities thereof required to produce the desired therapeutic results are too large to permit administration in a single dose. Furthermore, the ingredients are such that, if admixed in a single-portion dose, they interact in such a way as to adversely affect the stability of the formulation. Also, the formulation is administered in capsule form and, therefore, must normally be taken with water or some other fluid to facilitate swallowing.

SUMMARY OF THE INVENTION

It is a general object of the present invention to provide an improved therapeutic composition for the treatment of hangover, which avoids the disadvantages of prior formulations.

An important feature of the invention is the provision of a therapeutic composition for simultaneous treatment of all of the symptoms of hangover, and which can be administered in liquid form.

Another feature of the invention is the provision of a therapeutic composition of the type set forth, which may be taken in a single-portion dose and is characterized by stability and long shelf life.

In connection with the foregoing feature, it is another feature of the invention to provide a therapeutic composition of the type set forth, which includes acetaminophen along with antacid agents in a form to optimize effectiveness while not adversely affecting the acetaminophen.

Still another feature of the invention is the provision of a method for oral administration of a therapeutic composition of the type set forth.

Certain of these and other features of the invention are attained by providing a therapeutic composition for oral administration comprising, in suspension in a nontoxic therapeutically acceptable suspension medium, a finely powdered form of each of (a) a pain relieving amount of acetaminophen, and (b) an acid neutralizing and stomach settling amount of one or more mild antacid agents, such that the composition is basic and has a pH less than 9.

The invention consists of these and other novel features hereinafter fully described, and particularly pointed out in the appended claims, it being understood that various changes in the details may be made without departing from the spirit, or sacrificing any of the advantages of the present invention.

DESCRIPTION OF THE PREFERRED EMBODIMENT

The composition of the present invention includes four principal active ingredients: (1) an analgesic; (2) an antacid; (3) a stimulant; and (4) a rapidly available energy source. Aspirin and acetaminophen are both effective analgesics. Aspirin functions as an anti-inflammatory agent as well as an analgesic, but its anti-inflammatory properties are not needed in the treatment of hangover. Furthermore, aspirin has the disadvantages of exacerbating acid indigestion, which is one of the hangover symptoms to be treated, as well as irritating the stomach lining and potentially causing gastro-intestinal bleeding. Accordingly, in the present invention acetaminophen is used as the sole analgesic.

Heretofore, it has been thought that acid indigestion was one of the principal manifestations of hangover. Consequently, formulations for treating hangover have typically contained a strong antacid agent, such as magnesium hydroxide. This has resulted in very high pH formulations, which tend to degrade acetaminophen, resulting in unacceptably short shelf life of compositions which include acetaminophen. One solution to this problem was separation of the acetaminophen and the strong antacid into separate capsules, and is disclosed in the aforementioned U.S. Pat. No. 3,829,569. But that solution is attended by more complicated and expensive manufacture and inconvenient usage.

Applicants have determined that acid indigestion is not as significant a symptom of overindulgence in alcohol as had been previously thought. Rather, what is sometimes characterized as acid indigestion is more accurately described as queasiness and occasional diarrhea. Thus, a significant aspect of the present invention is the provision of a hangover treatment composition in which the selection, proportions, particle size and physical characteristics of the antacid agents is such as to provide sufficient acid neutralizing capacity to be effective in treating minor conditions of acid indigestion or mild stomach acidity, and also provide marked improvement in treating queasiness and diarrhea. This has made it possible to significantly reduce the pH of the composition while permitting it to be provided in a suspension form which accelerates and enhances the therapeutic action of the ingredients.

A composition effective in treating all of the major hangover symptoms requires, in addition to analgesic and antacid agents, active ingredients which provide other therapeutic effects. These ingredients include a stimulant to induce alertness, a quickly available carbohydrate to provide a source of energy, and a stomach protectant or adsorbent. There must also be provided a suitable suspension medium and it is also desirable that the composition be pleasant tasting.

A formulation which provides the foregoing effects and which has been found to produce excellent results in relieving the symptoms of overindulgence in alcohol is set forth in the following Example:

EXAMPLE I

| Substance | Function | Amount in Parts By Weight ±10% |
| --- | --- | --- |
| Acetaminophen | Analgesic | 8.0 |
| Magnesium trisilicate | Antacid, stomach protectant, adsorbent | 6 |

EXAMPLE I-continued

| Substance | Function | Amount in Parts By Weight ±10% |
|---|---|---|
| Calcium citrate, pulverized to a fine powder | Antacid, calcium source | 10 |
| Calcium carbonate, light precipitated powder | Antacid | 2.8 |
| Caffeine, anhydrous | Stimulant | 1.6 |
| Methylparaben | Preservative | 0.216 |
| Propylparaben | Preservative | 0.024 |
| Dextrose | Sweetener, energy source | 32 |
| Glycerin | Suspension medium, solvent, sweetener | 50.48 |
| Xanthan gum | Suspending agent, thickener | 0.24 |
| Spearmint oil | Stomachic, flavorant | 1.1052 |
| Caramel | Colorant | 0.4 |
| Purified water | Suspension medium, solvent, diluent | 40 |

The specific formulation set forth above produces optimal therapeutic results within the permissible deviation indicated. However, certain individual ingredients may vary in amount, one at a time, over a wider range and still produce an efficacious composition. It may also be possible to vary the amounts of more than one ingredient at a time as long as the pH of the resulting composition does not fall outside a predetermined range, set forth hereinafter. For those ingredients which may vary beyond ±10%, the maximum ranges of variation are as follows:

TABLE 1

| Substance | Maximum Variation from Example I Amounts |
|---|---|
| Acetaminophen | +50%, −50% |
| Magnesium trisilicate | +50%, −50% |
| Calcium citrate | +50%, −50% |
| Calcium carbonate | +50%, −50% |
| Caffeine | +50%, −60% |
| Dextrose | +100%, −75% |
| Spearmint Oil | +100%, −50% |

While the dextrose can be increased 100% from the amount of Example I, this may require increasing the amount of water to prevent precipitation of the dextrose upon cooling of the composition.

The purified water in the composition of Example I serves as a diluent and may be added in any desired amount to produce the desired total volume of composition. The amount set forth in Example I is an amount which will result in an effective single dose having a volume of one tablespoon, i.e., 0.5 fluid ounce or approximately 15 ml. It will be appreciated that compositions with greater or lesser concentrations of the active ingredients could be used as long as a sufficient volume of the formulation is administered to deliver the effective amounts of the active ingredients. Those effective amounts are set forth in Table 2 for a 14.785 ml dose:

TABLE 2

| Substance | Amount (mg.)/ 14.785 ml Dose | % w/w |
|---|---|---|
| Acetaminophen | 1000 | 5.23 |
| Magnesium trisilicate | 750 | 3.93 |
| Calcium citrate, pulverized powder | 1250 | 6.54 |
| Calcium carbonate, light precipitated powder | 350 | 1.83 |
| Caffeine anhydrous | 200 | 1.05 |
| Methylparaben | 27 | 0.14 |
| Propylparaben | 3 | 0.02 |
| Dextrose | 4000 | 20.93 |
| Glycerin | 6310 | 33.02 |
| Xanthan gum | 30 | 0.16 |
| Spearmint oil | 138 | 0.72 |
| Liquid caramel | 50 | 0.26 |
| Purified water | 5000 | 26.17 |

In the composition of Example I the dextrose serves as a sweetener and as a source of energy. Any readily available carbohydrate may provide the source of energy, but a sugar is selected, since it serves as a sweetner in addition to providing an energy source. More complex sugars, such as sucrose and lactose, could be used, but do not break down as rapidly and are, therefore, not as rapid a source of energy as a monosaccharide, such as fructose or dextrose. But, fructose tends to change color more readily to an undesirable mud-brown color. Thus, dextrose is preferred, since it exhibits much less color shift. Whatever small color shift may be exhibited by the dextrose is masked by the caramel colorant. The methylparaben and propylparaben serve as anti-bacterial preservative agents. The spearmint oil serves as a mild stomachic, a flavorant and a breath freshening agent.

As indicated above, a significant aspect of the invention is that it utilizes a unique combination of mild antacid agents. No strong antacids, such as hydroxides, are used. The resulting composition is basic, but has a relatively low pH. More specifically, the pH of the composition is less than 9 and, preferably, in a range from about 8.2 to about 8.4 for the formulation of Example I. This results in minimal degradation of the acetaminophen, producing a composition with a stable shelf life in excess of two years. The unique combination of antacid agents is such that it also provides auxiliary therapeutic functions. Thus, the calcium citrate also serves as a calcium source, and the magnesium trisilicate also serves as a stomach protectant and adsorbent, as described below.

Another significant aspect of the invention is that the composition is in the form of a suspension, the suspending medium consisting essentially of the glycerin, the xanthan gum acting as a suspending agent and the purified water, with the admixture of the other ingredients suspended therein. This permits the composition to be administered in liquid form, obviating the use of an auxiliary fluid, such as water or the like, which is necessary with pills or capsules to facilitate swallowing and dissolution in the stomach. The active ingredients in the suspension of the present invention are available for immediate action in the person being treated. The glycerin also serves as a sweetener.

The antacid agents are provided in a powdered or micro-pulverized form so as to provide a relatively smooth suspension. In this regard, commercially available calcium citrate "powder" is actually in a granular form which produces an unsuitably gritty suspension. Accordingly, the calcium citrate is finely ground in a hammer mill. Indeed, all of the powdered ingredients, including the antacid agents, the acetaminophen and the caffeine, are provided in a finely powdered form with a particle size which will pass through a 325 mesh screen. Also, the fine grinding of the antacids affords a greatly increased surface area to facilitate immediate action. Furthermore, the suspended form of magnesium trisilicate permits that ingredient to act not only as an antacid, but also as a stomach protectant or coater and as an adsorbent of undesirable elements in the gastro-intestinal tract.

The suspension of the composition of Example I is preferably prepared in relatively large quantities. The method of preparation of one gallon of the composition of Example I is described in detail below, but it will be appreciated that larger quantities can be prepared by scaling up the amounts appropriately. The preparation is a four-part process.

In Part I, 7.68 gm of xanthan gum is weighed and dispersed in 0.213 lbs. of glycerin. This dispersion is then dissolved in 0.2 gal. of purified water, mixing continuously while adding the dispersion. The mixture is allowed to stand for a few hours to completely dissolve the gum. The resulting product is a pale white, translucent, smooth paste.

In Part II water-soluble ingredients are dissolved in water. More specifically, 6.912 gm. of methylparaben, 0.768 gm. of propylparaben and 2.256 lbs. of dextrose are dissolved in 0.133 gal. of purified Water and heated to the boiling point and allowed to cool. The resulting product is a solution which is clear and colorless when hot, and cloudy when cooled.

In Part III, non-soluble powdered ingredients ground to a 325 mesh particle size, are mixed together with glycerin. More specifically, 0.564 lbs. of acetaminophen, 0.423 lbs. of magnesium trisilicate, 0.705 lbs. of calcium citrate in pulverized powder form, 0.197 lbs. of calcium carbonate in light precipitated powder form, and 0.113 lbs. of caffeine are mixed with 3.345 lbs. of glycerin in a blender or colloid mill to make a smooth paste. Then 38.4 ml. of spearmint oil is added to the suspension and mixed to dissolve the spearmint oil. There results a chalky white, smooth paste with a pleasant spearmint aroma.

In Part IV, the xanthan gum paste from Part I is added to the suspension from Part III, and then mixed continuously in a blender while adding the solution from Part II. Then 12.8 gm. of liquid caramel is added and mixed into the suspension. Enough purified water is added to make one gallon, and the product is blended to make a uniform suspension. The resulting product is a caramel or coffee-colored suspension having a specific gravity between 1.20 and 1.21, a pH in the range from about 8.2 to about 8.4, an acid neutralizing capacity of from about 16 to about 18 meq. and with a total aerobic microbial count which does not exceed 100 per ml. and which meets the requirements of tests for absence of *Escherichia coli* and *Pseudomonas aeruginosa*.

The composition of Example I is administered orally in a single dose of one-half fluid ounce or one tablespoon, i.e., approximately 15 ml. The dosage may be repeated after four to six hours if symptoms persist.

From the foregoing, it can be seen that there has been provided an improved therapeutic composition for the treatment of the manifestations of hangover resulting from overindulgence in alcohol and a method of administration thereof, with the composition including acetaminophen and one or more antacid agents in a liquid suspension form with a pH which is mildly basic so as to provide effective therapeutic activity without degrading the acetaminophen.

We claim:

1. A therapeutic composition for oral administration comprising, in suspension in a non-toxic therapeutically acceptable suspension medium, a finely powdered form of each of
   (a) a pain relieving amount of acetaminophen, and
   (b) an acid neutralizing and stomach settling amount of one or more mild antacid agents, such that the composition is basic and has a pH less than 9.

2. The therapeutic composition of claim 1, wherein said antacid agents include one or more of magnesium trisilicate, calcium citrate and calcium carbonate.

3. The therapeutic composition of claim 1, and further comprising a carbohydrate energy source.

4. The therapeutic composition of claim 3, wherein said energy source is dextrose.

5. The therapeutic composition of claim 1, and further comprising a stomachic agent.

6. The therapeutic composition of claim 5, wherein said stomachic agent is spearmint oil.

7. The therapeutic composition of claim 1, and further comprising a stimulant.

8. A therapeutic composition of matter including the following ingredients present in the recited approximate parts by weight:

| Ingredient | Amount in Parts by Weight ±10% |
| --- | --- |
| Acetaminophen | 8.0 |
| Magnesium trisilicate | 6.0 |
| Calcium citrate | 10.0 |
| Calcium carbonate | 2.8 |
| Caffeine | 1.6 | said ingredients being suspended in a suspension medium including the following constituents present in the recited approximate parts by weight:

| Constituent | Amount in Parts by Weight ±10% |
| --- | --- |
| Glycerin | 50.48 |
| Xanthan gum | 0.24 |
| Purified Water | 40.0 | such that the composition is basic and has a pH less than 9.

9. The therapeutic composition of claim 8, and further comprising one or more anti-bacterial preservative agents.

10. The therapeutic composition of claim 9, wherein said preservative agents include approximately 0.216 parts by weight of methylparaben and approximately 0.024 parts by weight of propylparaben.

11. The therapeutic composition of claim 8, and further comprising a carbohydrate energy source.

12. The therapeutic composition of claim 11, wherein said energy source includes approximately 32.0 parts by weight of dextrose.

13. The therapeutic composition of claim 8, and further comprising approximately 1.1 parts by weight of spearmint oil.

14. The therapeutic composition of claim 8, and further comprising approximately 0.4 parts by weight of liquid caramel.

15. A method of treating the manifestations of overindulgence in alcohol comprising: orally administering to a patient in need of such treatment an effective amount of a pharmaceutical composition comprising, in suspension in a non-toxic therapeutically acceptable suspension medium, each of
  (a) a pain relieving amount of acetaminophen,
  (b) an acid neutralizing and stomach settling amount of one or more mild antacid agents,
  (c) an alertness inducing amount of caffeine, and
  (d) a readily metabolized carbohydrate energy source,
such that the composition is basic and has a pH less than 9.

16. The method of claim 15, wherein said composition is administered in a dose of approximately 15 ml.

17. The method of claim 15, wherein said antacid agents include one or more of magnesium trisilicate, calcium citrate and calcium carbonate.

18. The method of claim 17, wherein said antacid agents include each of magnesium trisilicate, calcium citrate and calcium carbonate, and said energy source includes dextrose.

19. The method of claim 18, wherein the ingredients are administered in approximately the following dosages:

| Ingredient | Dosage (mg) ±10% |
| --- | --- |
| Acetaminophen | 1000 |
| Magnesium trisilicate | 750 |
| Calcium citrate | 1250 |
| Calcium carbonate | 350 |
| Caffeine | 200 |
| Dextrose | 4000 |

20. The method of claim 15, wherein the composition includes a stomachic and flavorant agent.

* * * * *